(12) United States Patent
Matsumoto

(10) Patent No.: US 8,270,570 B2
(45) Date of Patent: Sep. 18, 2012

(54) X-RAY IMAGE DIAGNOSIS APPARATUS AND CONTROL METHOD

(75) Inventor: Shinichi Matsumoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 119 days.

(21) Appl. No.: 12/497,985

(22) Filed: Jul. 6, 2009

(65) Prior Publication Data

US 2010/0027752 A1 Feb. 4, 2010

(30) Foreign Application Priority Data

Jul. 31, 2008 (JP) ................................. 2008-198619

(51) Int. Cl.
*H05G 1/56* (2006.01)
*H05G 1/58* (2006.01)
*H05G 1/54* (2006.01)

(52) U.S. Cl. .......................... 378/115; 378/101; 378/117

(58) Field of Classification Search .................. 378/101, 378/114, 115, 117
See application file for complete search history.

(56) References Cited

U.S. PATENT DOCUMENTS

| | | | | |
|---|---|---|---|---|
| 4,739,480 A * | 4/1988 | Oono et al. | .................... | 250/584 |
| 5,231,651 A * | 7/1993 | Ozaki et al. | ........................ | 378/4 |
| 6,508,586 B2 * | 1/2003 | Oota | .............................. | 378/196 |
| 7,177,393 B2 * | 2/2007 | Kanemitsu | ..................... | 378/117 |
| 7,341,375 B2 * | 3/2008 | Zaiki | .............................. | 378/196 |
| 7,356,121 B2 * | 4/2008 | Schwarz | ......................... | 378/101 |
| 7,508,915 B2 * | 3/2009 | Amitani et al. | .............. | 378/98.8 |
| 7,706,505 B2 * | 4/2010 | Tachikawa | .................... | 378/98.8 |
| 7,783,009 B2 * | 8/2010 | Bielski et al. | ................. | 378/117 |
| 8,000,510 B2 * | 8/2011 | Boeing et al. | ................. | 382/128 |
| 2004/0066900 A1 * | 4/2004 | Motoki | ......................... | 378/116 |
| 2004/0125920 A1 * | 7/2004 | Zaiki | ............................. | 378/195 |
| 2008/0247513 A1 * | 10/2008 | Amitani et al. | ................. | 378/95 |

FOREIGN PATENT DOCUMENTS

JP 2006-325956 12/2006

* cited by examiner

*Primary Examiner* — Thomas R Artman
(74) *Attorney, Agent, or Firm* — Fitzpatrick, Cella, Harper & Scinto

(57) ABSTRACT

An X-ray image diagnosis apparatus which can accept operations from a plurality of operation panels can ensure convenience for operators while avoiding the risk of excessively exposing an object to X-rays. This invention is a control method in an X-ray image diagnosis apparatus which irradiates an object with X-rays and processes a captured image obtained by imaging the object. This method includes the steps of receiving information associated with an imaging condition at the time of X-ray irradiation which is input via an operation panel, discriminating, when the information associated with the imaging condition is received, an operation panel from which the information associated with the imaging condition has been input, and restricting, when the information associated with the imaging condition is received, the reception of a specific instruction input via an operation panel other than the discriminated operation panel.

20 Claims, 8 Drawing Sheets

X-RAY IMAGE DIAGNOSIS APPARATUS AND CONTROL METHOD

BACKGROUND OF THE INVENTION

1. Field of the Invention

The present invention relates to a control technique in an X-ray image diagnosis apparatus.

2. Description of the Related Art

Recently, in the field of X-ray image diagnosis apparatuses for medical use, apparatuses of the digital image scheme have become mainstream in place of those of the conventional analog imaging scheme. For example, the digital image scheme allows continuously captured digital images to be displayed as moving images and stored in a memory and a hard disk drive. This advantageously provides ease of use in performing diagnosis, medical treatments, and the like.

In general, an X-ray image diagnosis apparatus of the digital image scheme includes an imaging apparatus body which irradiates X-rays and generates radiographed images based on data read from a sensor panel. This apparatus also includes an operation panel to input imaging conditions to be set in the imaging apparatus body and issue an X-ray irradiation instruction to the imaging apparatus body.

In addition, it is possible to form a network system by connecting, to the imaging apparatus body, a monitor cart to store/display generated captured images and input patient information.

Forming such a system makes it also possible to input imaging conditions and an X-ray irradiation instruction via the operation panel provided on the monitor cart.

In the network system formed in this manner, when control operations are performed from a plurality of operation panels, the contents of the control operations from the respective operation panels are evenly sent to the imaging apparatus body. The imaging apparatus body is then controlled to sequentially perform processing in accordance with the order in which the control operations have been performed.

Alternatively, as disclosed in Japanese Patent Laid-Open No. 2006-325956, providing an operation unit selection button or the like to explicitly switch an operation panel having an operation right makes it possible to perform control so as to make only one operation panel permanently effective.

In the case of a network system having a plurality of operation panels connected to an imaging apparatus body, doctors or technicians often perform control operations via different operation panels from the respective standpoints.

In this case, since the imaging apparatus body simultaneously accepts control operations such as the input of X-ray irradiation start instructions and imaging conditions (a dose of X-rays, frame rate, irradiation field, and the like) from a plurality of operation panels, the apparatus body may start imaging under unintended imaging conditions. That is, there is a risk that an object to be examined may be excessively exposed to X-rays.

In contrast, configuring this system to set an operation right and make an operable operation panel permanently effective will prohibit any control operations from operation panels having no operation right. This will lead to deterioration in operation efficiency and a delay in taking action in an emergency.

SUMMARY OF THE INVENTION

The present invention has been made in consideration of the above problem.

An X-ray image diagnosis apparatus according to the present invention has the following arrangement. That is, an X-ray image diagnosis apparatus which irradiates an object with X-rays and processes a radiographed image obtained by imaging the object, the apparatus comprising: a reception unit configured to receive information associated with an imaging condition at the time of X-ray irradiation which is input via an operation panel; a discrimination unit configured to discriminate, when the reception unit receives the information associated with the imaging condition, an operation panel from which the information associated with the imaging condition has been input; and a restriction unit configured to restrict, when the reception unit receives the information associated with the imaging condition, reception of a specific instruction input via an operation panel other than the operation panel discriminated by the discrimination unit.

A control method according to the present invention comprises the following steps.

That is, a control method being for application to an X-ray image diagnosis apparatus which irradiates an object with X-rays and processes a radiographed image obtained by imaging the object, the method comprising steps of: receiving information associated with an imaging condition at the time of X-ray irradiation which is input via an operation panel; discriminating, when the information associated with the imaging condition is received in the step of receiving, an operation panel from which the information associated with the imaging condition has been input; and restricting, when the information associated with the imaging condition is received in the step of receiving, reception of a specific instruction input via an operation panel other than the operation panel discriminated in the step of discriminating.

According to the present invention, the X-ray image diagnosis apparatus capable of accepting control operations from a plurality of operation panels can ensure convenience for operators while avoiding the risk of excessively exposing an object to X-rays.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Embodiments of the present invention will now be described in detail in accordance with the accompanying drawings.

[First Embodiment]
<1. Overall Arrangement of X-Ray Image Diagnosis Apparatus>

Figure 1:
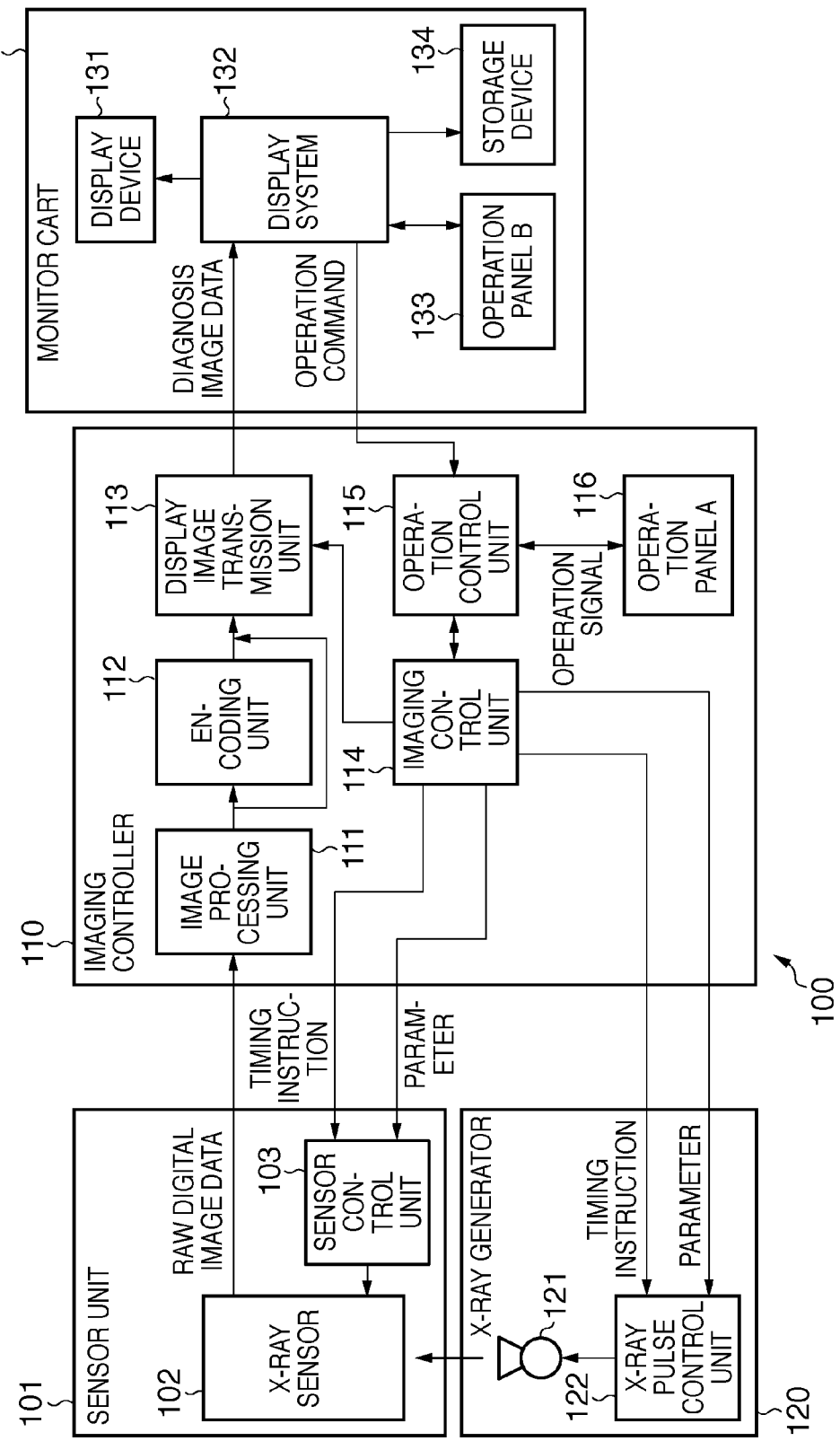
FIG. 1 is a block diagram showing the overall arrangement of an X-ray image diagnosis apparatus according to an embodiment of the present invention.

FIG. 1 is a block diagram showing the overall arrangement of an X-ray image diagnosis apparatus according to an embodiment of the present invention.

As shown in FIG. 1, an X-ray image diagnosis apparatus 100 according to this embodiment includes a sensor unit 101, an X-ray generator 120, an imaging controller 110, and a monitor cart 130.

The sensor unit 101 includes an X-ray sensor 102 and a sensor control unit 103. The X-ray sensor 102 includes, for example, a unit formed from a solid-state imaging device which senses X-rays and outputs an electrical signal corresponding to the intensity of the detected X-rays. Alternatively, the sensor unit includes a unit formed by combining a phosphor which generates fluorescence corresponding to the energy of X-rays and a photoelectric conversion element which converts the fluorescence into an electrical signal corresponding to the intensity of visible light.

The raw digital image data output from the X-ray sensor 102 is transmitted to the imaging controller 110.

The sensor control unit 103 drives/controls the X-ray sensor 102. More specifically, the sensor control unit 103 generates a timing signal defining the timing of data output of the X-ray sensor 102 in accordance with a timing instruction from an imaging control unit 114 (to be described later). The sensor control unit 103 also performs output mode setting processing for the X-ray sensor 102 in accordance with a parameter from the imaging control unit 114.

Assume that a fast digital interface such as LVDS (Low Voltage Differential Signaling) is used for the transmission of raw digital image data between the sensor unit 101 and the imaging controller 110. In addition, asynchronous serial communication such as UART is used to input and output timing instructions and parameters.

The X-ray generator 120 includes an X-ray tube 121 and an X-ray pulse control unit 122. The X-ray tube 121 irradiates pulse X-rays in accordance with a timing signal from the X-ray pulse control unit 122. The X-ray pulse control unit 122 outputs a timing signal defining an X-ray irradiation timing for the X-ray tube 121 under imaging conditions set based on a timing instruction and parameters from the imaging control unit 114 (to be described later).

Assume that asynchronous serial communication or a low-delay network protocol such as CAN is used for the input/output of timing instructions and parameters between the X-ray generator 120 and the imaging controller 110. Note that CAN is an abbreviated expression of Controller Area Network.

The imaging controller 110 includes an image processing unit 111, an encoding unit 112, a display image transmission unit 113, the imaging control unit 114, an operation control unit 115, and an operation panel A 116.

The imaging controller 110 can continuously obtain images by continuously transmitting timing instructions to the X-ray generator 120 and the sensor unit 101. For example, the imaging controller 110 can generate moving image data at 30 fps by transmitting 30 timing instructions per sec.

The image processing unit 111 performs predetermined image processing for raw digital image data transmitted from the sensor unit 101. More specifically, the image processing unit 111 performs, for example, correction processing or noise removal processing dependent on the characteristics of the X-ray sensor 102, or quality enhancement processing such as dynamic range improvement.

The raw digital image data having undergone image processing is sent to the encoding unit 112. Note that if encoding is not to be performed, the data is directly sent to the display image transmission unit 113.

The encoding unit 112 performs lossless compression encoding processing for the raw digital image data having undergone image processing, and then sends the raw digital image data to the display image transmission unit 113.

The display image transmission unit 113 transmits the raw digital image data having undergone compression encoding processing as diagnosis image data to the monitor cart 130.

Assume that a network using Gigabit Ethernet® used for the transmission of diagnosis image data connects the imaging controller 110 and the monitor cart 130. For this reason, the display image transmission unit 113 transmits the diagnosis image data to the monitor cart 130 upon executing packetization processing and network protocol processing for the data.

The imaging control unit 114 and the operation control unit 115 each include a microprocessor, a ROM (Read Only Memory) storing control programs, and a RAM (Random Access Memory) used as a work area at the time of execution of a program. Each unit further includes an I/O port.

The operation control unit 115 accepts an operation signal corresponding to a control operation from the operation panel A 116, or accepts an operation command generated in correspondence with a control operation on the operation panel B 133 via a network.

The imaging control unit 114 outputs an imaging start/stop instruction in accordance with an operation signal or operation command accepted by the operation control unit 115, or outputs parameters for setting imaging conditions in the sensor unit 101 and the X-ray generator 120. The imaging control unit 114 also outputs timing instructions. The details of processing in the imaging control unit 114 and operation control unit 115 will be described later with reference to FIG. 3.

The operation panel A 116 includes a touch panel and a dedicated monitor. When an operator touches an area corresponding to a graphic button or icon displayed on the monitor with a pen or finger (performs a control operation), the operation panel A 116 designates the operation of the X-ray image diagnosis apparatus 100. The operation panel A 116 is connected to the operation control unit 115 via an interface such as DVI or USB.

The monitor cart 130 includes a PC (Personal Computer) and peripheral devices connected thereto. More specifically, the monitor cart 130 includes a display system 132, a display device 131, an operation panel B 133, and a storage device 134.

The display system 132 is constituted by a PC main body and application software operating on the PC. The display system 132 receives the diagnosis image data transmitted from the imaging controller 110 via a network. If the diagnosis image data has been encoded, the display system 132 outputs the data to the display device 131 upon decoding it. In addition, the display system 132 can store the diagnosis image data in the storage device 134, generate an operation command corresponding to a control operation on the operation panel B 133, and transfer the command to the imaging controller 110 via the network.

The display device 131 is a live monitor for displaying the diagnosis image data transmitted from the imaging controller 110, and is connected to the display system 132 via a DVI interface.

The operation panel B 133 includes a membrane keyboard having dedicated buttons arranged thereon, a general-purpose keyboard for a PC, a mouse, and an operation monitor. Like the operation panel A 116, the operation panel B 133 can designate the operation of the X-ray image diagnosis apparatus 100 by performing a control operation.

<2. Display Window Displayed on Operation Panel A or B>

Figure 2:
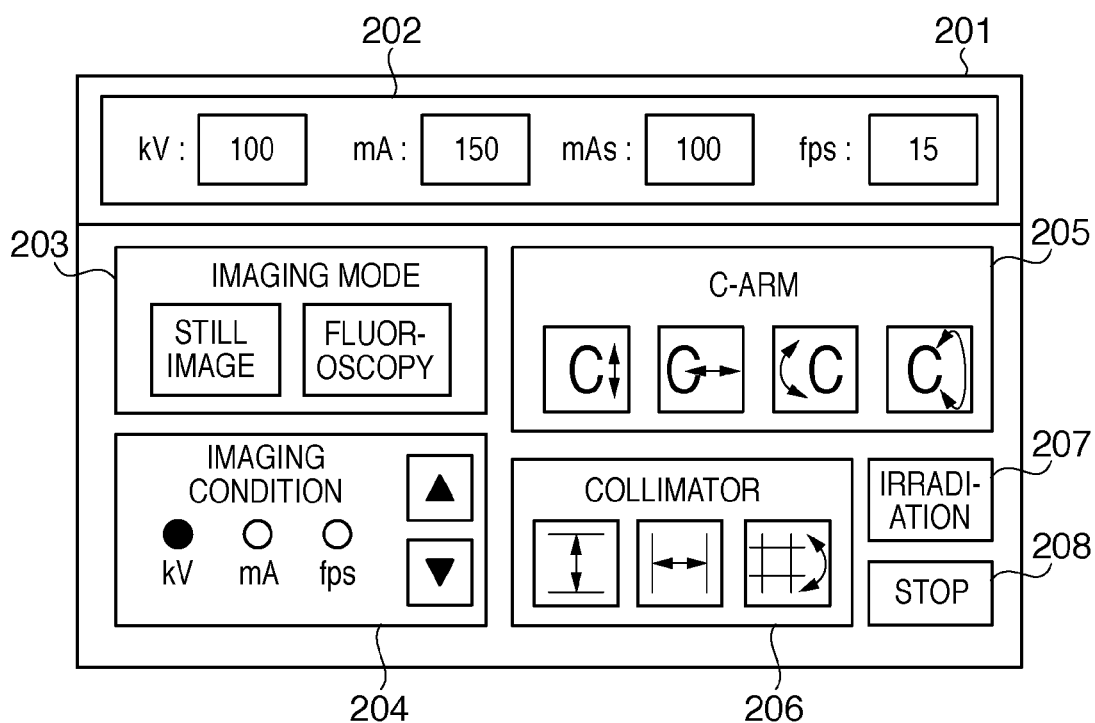
FIG. 2 is a view showing an example of a display window displayed on a monitor forming an operation panel A 116 or operation panel B 133.

FIG. 2 is a view showing an example of the display window displayed on a monitor forming the operation panel A 116 or operation panel B 133.

Referring to FIG. 2, reference numeral 201 denotes the entire area of a monitor screen. This area has a resolution of VGA (640×480 dots).

Reference numeral 202 denotes an area for displaying the currently set numerical values of imaging conditions. In this area, the respective values including a kV value (tube voltage value), mA value (tube current value), mAs value (tube current-time product value), and fps value (frame rate) are displayed from the left to the right. When a control operation is performed to input an imaging condition, the corresponding displayed value in the area 202 changes accordingly.

Reference numeral 203 denotes an imaging mode selection area including a "still image button" and a "fluoroscopy button". Selecting one of these buttons can designate the still image radiography mode or the fluoroscopic radiography mode as an imaging mode.

Reference numeral 204 denotes an area for inputting imaging conditions. This area includes radio buttons each for selecting a type of imaging condition (a tube current value, tube voltage value, or frame rate) and upward and downward arrow buttons for changing the value of a selected imaging condition. When an imaging condition is selected, the corresponding radio button is displayed in black. Selecting an imaging condition and pressing the upward and downward arrow buttons to increase/decrease the numerical value can input the imaging condition. Input numerical values are sequentially displayed in the area 202 described above.

Reference numeral 205 denotes an area for displaying a C-arm control button. The X-ray image diagnosis apparatus 100 has the sensor unit 101 and the X-ray tube 121 mounted on the two ends of an arm in the form of the letter "C". Moving and rotating this arm by arbitrary amounts can radiograph the object at various positions and angles.

In the area 205, buttons for moving the arm in the vertical and horizontal directions, changing the vertical angle of the arm, and controlling the rotation of the arm in the axial direction are arranged from the left to the right. Pressing these buttons can operate a motor incorporated in the C-arm to move and rotate the arm.

Reference numeral 206 denotes an area for displaying collimator stop control buttons. The collimator is a stop device for changing the shape and size of an X-ray irradiation field. In the area 206, buttons for performing vertical stop control, horizontal stop control, and irradiation area control are arranged from the left to the right.

Reference numeral 207 denotes an irradiation start instruction button; and 208, an irradiation stop instruction button. When the operator presses the irradiation start instruction button 207, the apparatus starts imaging based on the set imaging conditions.

When the operator presses the irradiation stop instruction button 208, the apparatus stops imaging. This embodiment uses the buttons displayed on the operation panel to issue these imaging start and stop instructions. However, the present invention is not limited to this. For example, the apparatus can be configured to issue imaging start and stop instructions by using, for example, discrete foot switches, hand switches, and membrane switches. In addition, the buttons for issuing imaging start and stop instructions may be integrated into one button or switch instead of including discrete buttons. Assume that in this case, the apparatus performs imaging while the operator keeps pressing the button, and stops imaging at the same time when the operator releases the button.

<3. Control Processing Sequence in X-Ray Image Diagnosis Apparatus>

Figure 3:
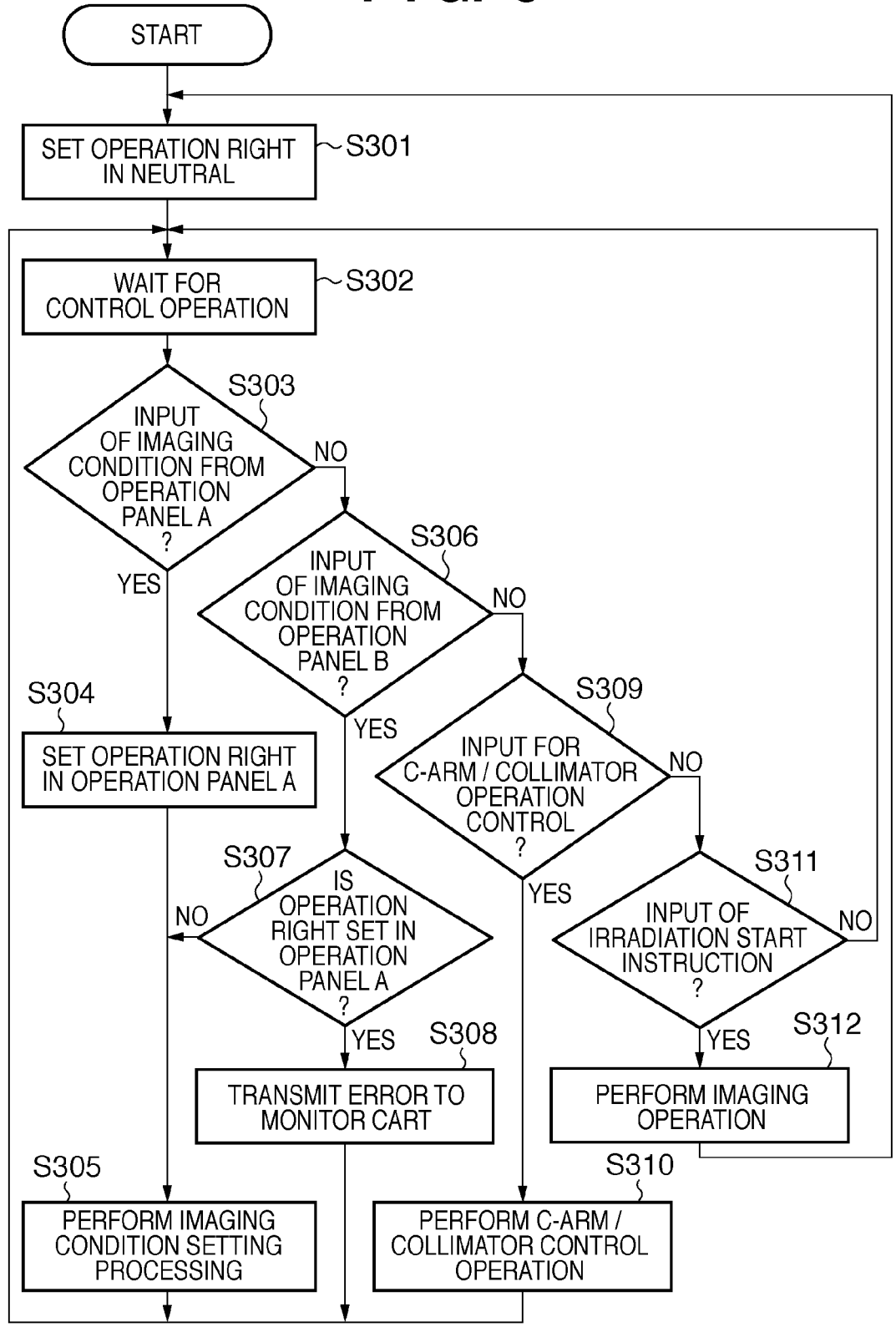
FIG. 3 is a flowchart showing a control processing sequence in an X-ray image diagnosis apparatus 100.

A control processing sequence in the X-ray image diagnosis apparatus 100 will be described next with reference to FIG. 3. FIG. 3 is a flowchart showing a control processing sequence in the X-ray image diagnosis apparatus 100. Note that this flowchart is implemented by causing a microprocessor to execute control programs which are stored in the ROM and implement the imaging control unit 114 and the operation control unit 115.

In step S301, the microprocessor executes the processing of setting the operation right in neutral. The operation right is the right to operate the imaging control unit 114 by performing a specific control operation (inputting imaging conditions and an irradiation start instruction). The state in which the operation right is set in neutral is the state in which the imaging control unit 114 operates in accordance with a control operation on either of the two operation panels (the operation panel A 116 and the operation panel B 133).

In step S302, the microprocessor waits for a control operation by the operator on an operation panel. More specifically, the operation control unit 115 executes the processing of waiting for the transmission of an operation signal from the operation panel A 116 or an operation command from the display system 132.

When the operator performs a control operation on the operation panel A 116 or the operation panel B 133 in step S302, the process advances to step S303.

In step S303, the microprocessor determines whether the operation is a control operation on the operation panel A 116 and the control operation is the input of an imaging condition. More specifically, the operation control unit 115 determines whether the input is an operation signal generated in accordance with a control operation on each button in the imaging condition area 204 displayed on the monitor forming the operation panel A 116.

If the microprocessor determines that the operation is a control operation on the operation panel A 116 and the control operation is the input of an imaging condition, the process advances to step S304.

In step S304, the operation control unit 115 performs the processing of setting the operation right in the operation panel A 116. In the state in which the operation right is set in the operation panel A 116, the operator cannot input any imaging condition (any control operation on the buttons arranged in the imaging condition area 204) or any irradiation start instruction from another operation panel (the operation panel B 133). That is, even if an operation command corresponding to the input of an imaging condition and irradiation start instruction from the operation panel B 133 is transmitted, the operation control unit 115 rejects the reception of the operation command.

In step S305, the imaging control unit 114 executes the processing of setting the input imaging condition. An imaging condition is set by transmitting a parameter to the sensor unit 101 and X-ray generator 120 connected to the imaging controller 110.

If the microprocessor determines in step S303 that the control operation on the operation panel A 116 is not the input of any imaging condition from the operation panel A 116, the process advances to step S306.

The microprocessor checks in step S306 whether the operation is the input of an imaging condition from the operation panel B 133. More specifically, the operation control unit 115 checks whether the input is a transmitted operation command corresponding to the input of an imaging condition from the operation panel B 133 of the monitor cart 130.

If the microprocessor determines as a result of the check that the operation is the input of an imaging condition from the operation panel B 133, the process advances to step S307. In step S307, the operation control unit 115 checks the current set state of the operation right. If the microprocessor determines as a result of the check in step S307 that the operation right is set in the operation panel A 116, the microprocessor rejects the acceptance of an operation command corresponding to the input of an imaging condition from the operation panel B 133.

In this case, in step S308, the operation control unit 115 performs the processing of transmitting an error command to the monitor cart 130 via the network.

If the microprocessor determines in step S307 that the operation right is not set in the operation panel A 116, that is, the operation right is set in the operation panel B 133, the process advances to step S305. In step S305, the imaging control unit 114 executes the processing of setting the input imaging condition.

If the microprocessor determines in step S306 that the input is not the input of an imaging condition from the operation panel B 133, the process advances to step S309.

In step S309, the microprocessor determines whether the input is an input for C-arm/collimator operation control. More specifically, the operation control unit 115 checks whether the input is an operation signal corresponding to a control operation on each button in the area 205 or 206 displayed on the monitor forming the operation panel A 116. Alternatively, the operation control unit 115 checks whether the input is an operation command transmitted by performing a similar control operation on the operation panel B 133.

If the microprocessor determines as a result of the check in step S309 that the input is for C-arm/collimator operation control, the process advances to step S310 to execute C-arm/collimator control operation. More specifically, the microprocessor transmits control commands to the C-arm control motor and collimator connected to the imaging controller 110.

If the microprocessor determines as a result of the check in step S309 that the input is not for C-arm/collimator operation control, the process advances to step S311. In step S311, the operation control unit 115 checks whether the input is the input of an irradiation start instruction. If the operation control unit 115 determines that the input is the input of an irradiation start instruction, the process advances to step S312. In step S312, the imaging control unit 114 starts imaging.

If the microprocessor determines in step S311 that the input is not the input of an irradiation start instruction, the process returns to step S302 again to wait for a control operation on one of the operation panels.

As described with reference to FIG. 1, in step S312, the microprocessor drives the sensor unit 101 and the X-ray generator 120 under set imaging conditions to generate raw digital image data used for a moving or still image.

In addition, the microprocessor drives the image processing unit 111 to execute image processing for the raw digital image data, and drives the encoding unit 112 to execute encoding processing for the raw digital image data.

Furthermore, the microprocessor drives the display image transmission unit 113 to execute the processing of transmitting the encoded raw digital image data as diagnosis image data to the monitor cart 130. When imaging is complete, the process advances to step S301 to clear the set operation right and return its state to the neutral state again.

As described above, in the X-ray image diagnosis apparatus according to this embodiment, once an imaging condition is input from a predetermined operation panel, no imaging condition can be input from other operation panels. This makes it possible to avoid the setting of an unintended imaging condition.

Note that the apparatus allows control operations other than the input of an imaging condition, and hence ensures convenience for the operator.

<4. State Transition in X-Ray Image Diagnosis Apparatus>

Figure 4:
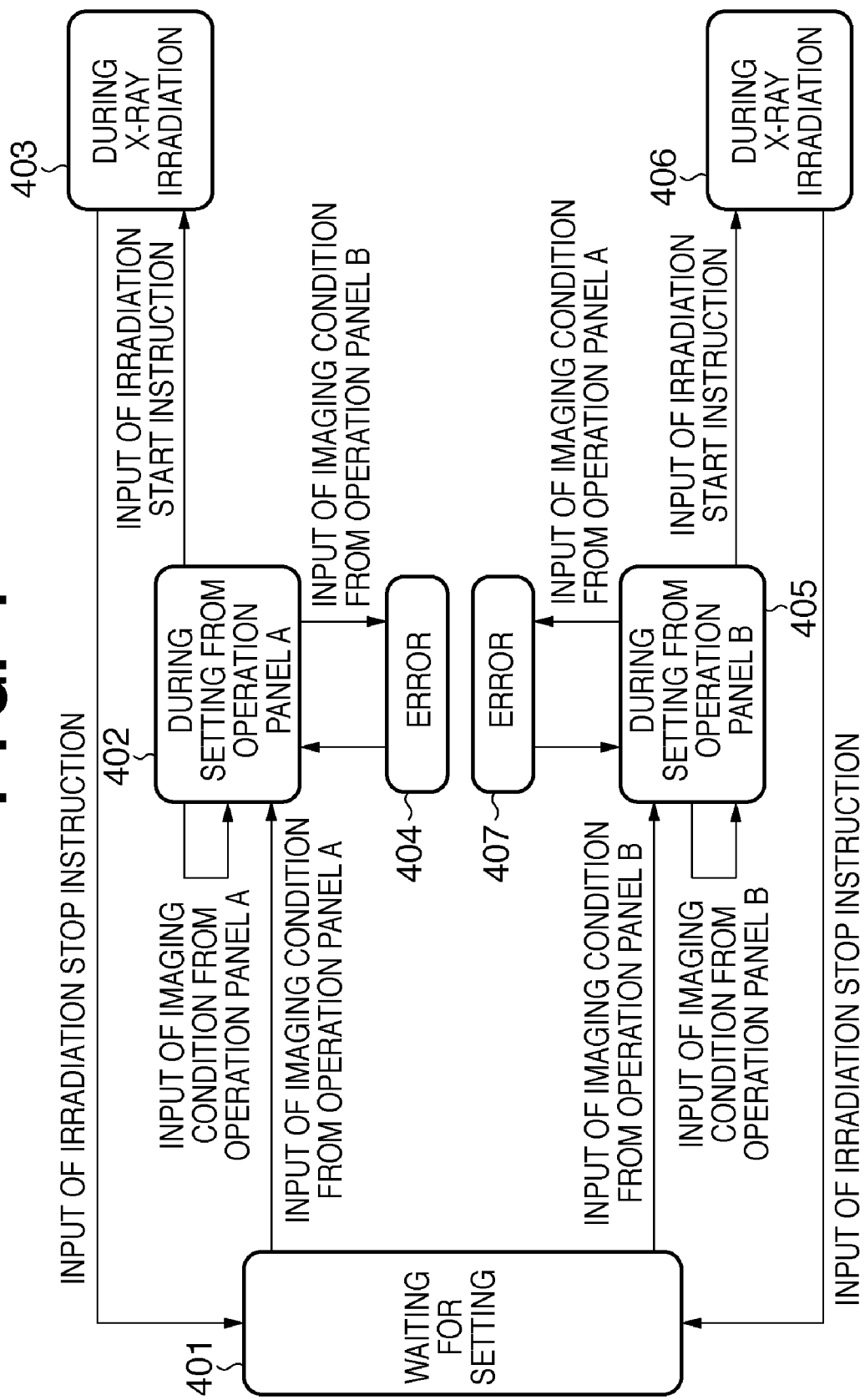
FIG. 4 is a view showing the state transition associated with control operations in the X-ray image diagnosis apparatus 100.

FIG. 4 is a view showing the state transition associated with control operations in the X-ray image diagnosis apparatus 100. Referring to FIG. 4, reference numeral 401 denotes a setting wait state. This is the state after the operation right is set in neutral in step S301 in FIG. 3.

In the setting wait state 401, when an imaging condition is input from the operation panel A 116 (step S303), the state transitions to a setting state 402.

In the setting state 402, the input of an imaging condition from the operation panel A 116 is normally processed. In contrast, the input of an imaging condition from the operation panel B 133 is not normally processed, and the state transitions to an error state 404. That is, step S308 is executed to transmit an error command to the monitor cart 130.

If an irradiation start instruction (step S311) is input in the setting state 402, the state transitions to an X-ray irradiating state 403. That is, the apparatus starts imaging (step S312). When imaging is complete, the state transitions to the setting wait state 401 again.

In the setting wait state 401, when an imaging condition is input from the operation panel B 133, the state transitions to the setting state 405. In this case, as in setting state 402, although the input of an imaging condition from the operation panel B 133 is normally processed, the input of an imaging condition from the operation panel A 116 is not normally processed. The state then transitions to an error state 407.

In addition, when an irradiation start instruction is issued in a setting state 405, the state transitions to an X-ray irradiating state 406. When imaging is complete, the state transitions to the setting wait state 401 again.

As is obvious from the above description, the X-ray image diagnosis apparatus according to this embodiment is configured to accept control operations on a plurality of operation panels. The apparatus is configured such that when an imaging condition is input, the apparatus accepts only an input from the operation panel from which the first imaging condition has been input, as long as the input is an imaging condition. The apparatus is also configured to accept a control operation other than the input of an imaging condition.

This makes it possible to avoid the situation in which the apparatus starts imaging under an unintended imaging condition.

Consequently, this can ensure convenience for operators while avoiding the risk of excessively exposing an object to X-rays.

[Second Embodiment]

The first embodiment is configured such that when an imaging condition is input, the apparatus restricts the input of an imaging condition from an operation panel other than the operation panel from which the imaging condition has been input. However, the present invention is not limited to this.

For example, the apparatus may be configured to restrict the input of an irradiation start instruction from an operation panel other than the operation panel from which an imaging condition has been input. The details of this embodiment will be described below.

<1. Control Processing Sequence in X-Ray Image Diagnosis Apparatus>

Figure 5A:
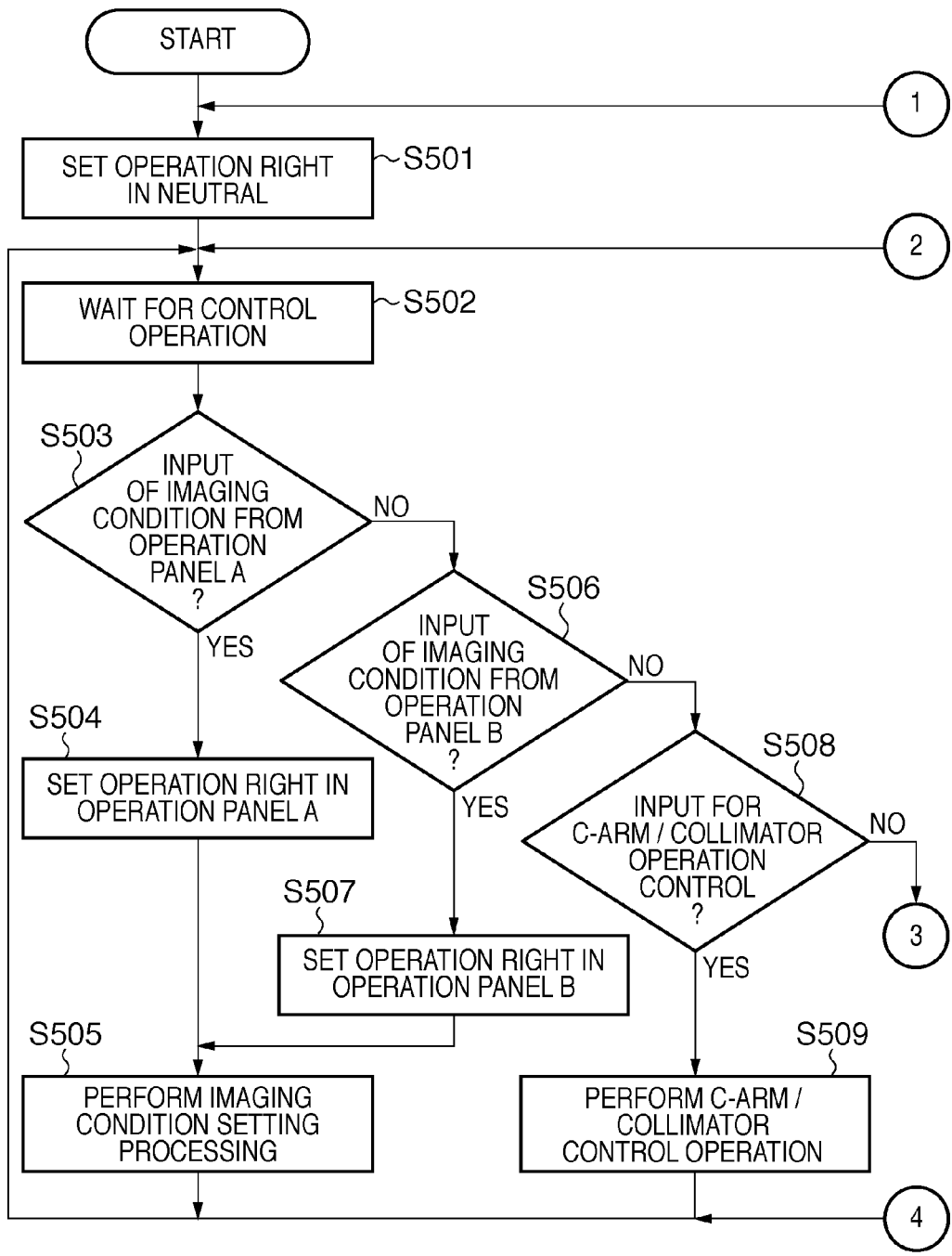
FIGS. 5A and 5B are flowcharts showing a control processing sequence in an X-ray image diagnosis apparatus according to the second embodiment of the present invention.
Figure 5B:
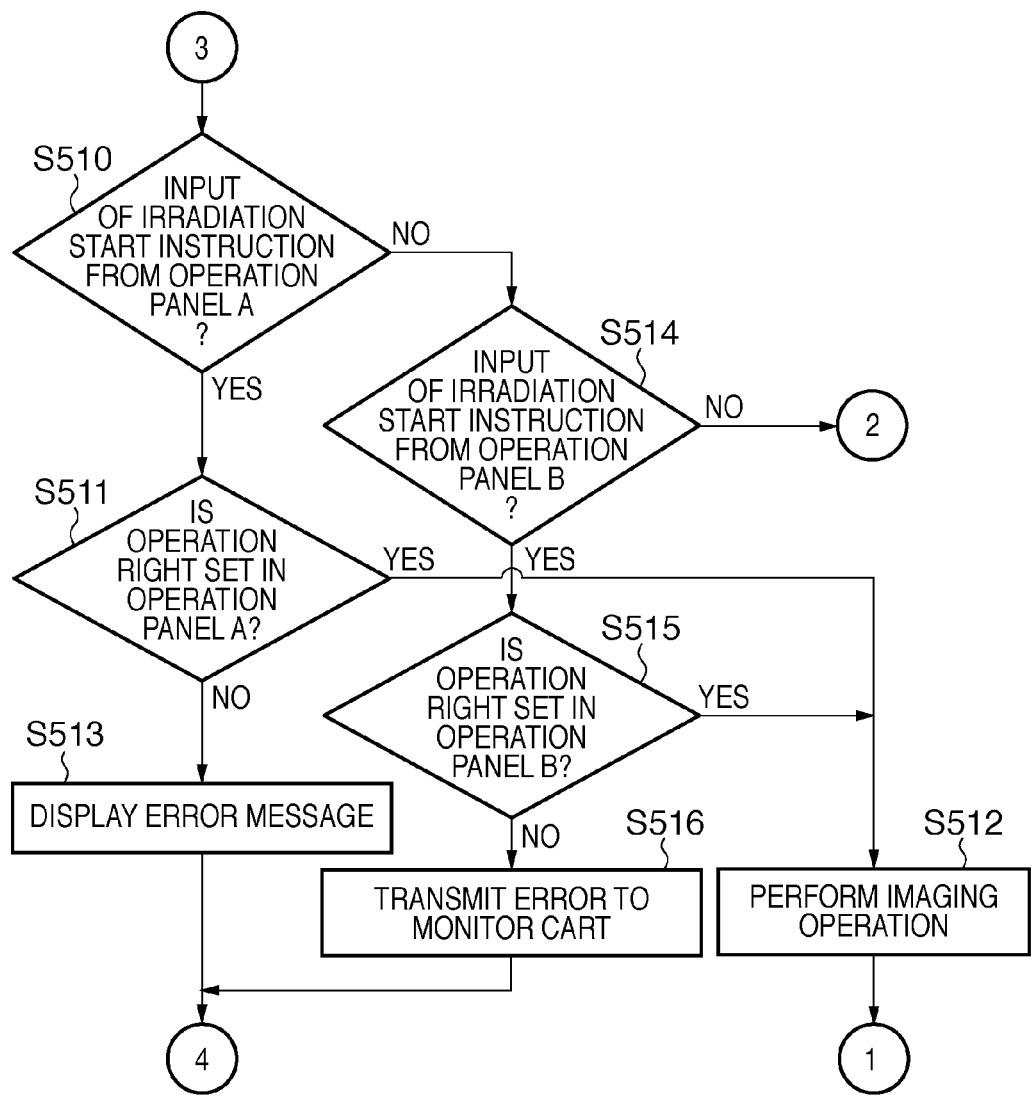

FIGS. 5A and 5B are flowcharts showing a control processing sequence in an X-ray image diagnosis apparatus 100 according to the second embodiment of the present invention. Note that this flowchart is implemented by causing a microprocessor to execute control programs which are stored in the ROM and implement an imaging control unit 114 and an operation control unit 115.

In step S501, the microprocessor executes the processing of setting the operation right in neutral.

In step S502, the microprocessor waits for a control operation by the operator on an operation panel. More specifically, the operation control unit 115 executes the processing of waiting for the transmission of an operation signal from an operation panel A 116 or an operation command from a display system 132.

When control operation is performed on the operation panel A 116 or the operation panel B 133 in step S502, the process advances to step S503.

In step S503, the microprocessor determines whether the operation is a control operation on the operation panel A 116 and the control operation is the input of an imaging condition. More specifically, the operation control unit 115 determines whether the input is an operation signal generated in accordance with a control operation on each button in an imaging condition area 204 displayed on the monitor forming the operation panel A 116.

If the microprocessor determines that the operation is a control operation on the operation panel A 116 and the control operation is the input of an imaging condition, the process advances to step S504.

In step S504, the operation control unit 115 performs the processing of setting the operation right in the operation panel A 116. In the state in which the operation right is set in the operation panel A 116, the operator cannot input any irradiation start instruction from another operation panel (the operation panel B 133). That is, even if an operation command corresponding to the input of an irradiation start instruction from the operation panel B 133 is transmitted, the operation control unit 115 rejects the reception of the operation command.

In step S505, the imaging control unit 114 executes the processing of setting the input imaging condition. An imaging condition is set by transmitting a parameter to a sensor unit 101 and X-ray generator 120 connected to an imaging controller 110.

If the microprocessor determines in step S503 that the control operation on the operation panel A 116 is not the input of any imaging condition, the process advances to step S506.

The microprocessor checks in step S506 whether the operation is the input of an imaging condition from an operation panel B 133. More specifically, the operation control unit 115 checks whether the input is a transmitted operation command corresponding to the input of an imaging condition which is performed on the operation panel B 133 of a monitor cart 130.

If the microprocessor determines as a result of the check that the operation is the input of an imaging condition from the operation panel B 133, the process advances to step S507. In step S507, the operation control unit 115 executes the processing of setting the operation right in the operation panel B 133. Furthermore, in step S505, the imaging control unit 114 executes the processing of setting an imaging condition.

If the microprocessor determines in step S506 that the operation is not the input of any imaging condition from the operation panel B 133, the process advances to step S508.

In step S508, the microprocessor determines whether the input is an input for C-arm/collimator operation control. More specifically, the operation control unit 115 checks whether the input is an operation signal corresponding to a control operation on each button in an area 205 or 206 displayed on the monitor forming the operation panel A 116. Alternatively, the operation control unit 115 checks whether the input is an operation command transmitted by performing a similar control operation on the operation panel B 133.

If the microprocessor determines as a result of the check in step S508 that the input is for C-arm/collimator operation control, the process advances to step S509 to execute a C-arm/collimator control operation. More specifically, the microprocessor transmits control commands to the C-arm control motor and collimator connected to the imaging controller 110.

If the microprocessor determines as a result of the check in step S508 that the input is not for C-arm/collimator operation control, the process advances to step S510.

In step S510, the operation control unit 115 checks whether the input is the input of an irradiation start instruction. More specifically, the operation control unit 115 determines whether the input is an operation signal corresponding to the input of an irradiation start instruction from the operation panel A 116. If the operation control unit 115 determines that the input is the input of an irradiation start instruction from the operation panel A 116, the process advances to step S511.

In step S511, the operation control unit 115 checks whether the current operation right is set in the operation panel A 116. If the operation control unit 115 determines as a result of the check in step S511 that the operation right is not set in the operation panel A 116, that is, the operation right is set in the operation panel B 133, the process advances to step S513.

In step S513, the operation control unit 115 rejects the reception of an operation signal corresponding to the input of an irradiation start instruction from the operation panel A 116, and displays an error message on the monitor forming the operation panel A 116.

If the operation control unit 115 determines in step S511 that the operation right is set in the operation panel A 116, the process advances to step S512.

In step S512, the imaging control unit 114 starts imaging. Note that imaging is the same as that in step S312 in FIG. 3. When imaging is complete, the process returns to step S501.

If the operation control unit 115 determines in step S510 that the input is not the input of an irradiation start instruction from the operation panel A 116, the process advances to step S514. In step S514, the operation control unit 115 checks whether the input is the input of an irradiation start instruction from the operation panel B 133. More specifically, the operation control unit 115 determines whether the input is an operation command transmitted in accordance with the input of an irradiation start instruction from the operation panel B 133. If the operation control unit 115 determines in step S514 that the input is the input of an irradiation start instruction from the operation panel B 133, the process advances to step S515.

In step S515, the operation control unit 115 checks whether the current operation right is set in the operation panel B 133. If the operation control unit 115 determines as a result of the check in step S515 that the operation right is not set in the operation panel B 133, the process advances to step S516.

In step S516, the operation control unit 115 rejects the reception of an operation command corresponding to the input of an irradiation start instruction from the operation panel B 133, and transmits an error command to the monitor cart 130 via a network.

If the operation control unit 115 determines as a result of the check in step S515 that the operation right is set in the operation panel B 133, the process advances to step S512, in which the imaging control unit 114 starts imaging. When imaging is complete, the process returns to step S501 again.

<2. State Transition in X-Ray Image Diagnosis Apparatus>

Figure 6:
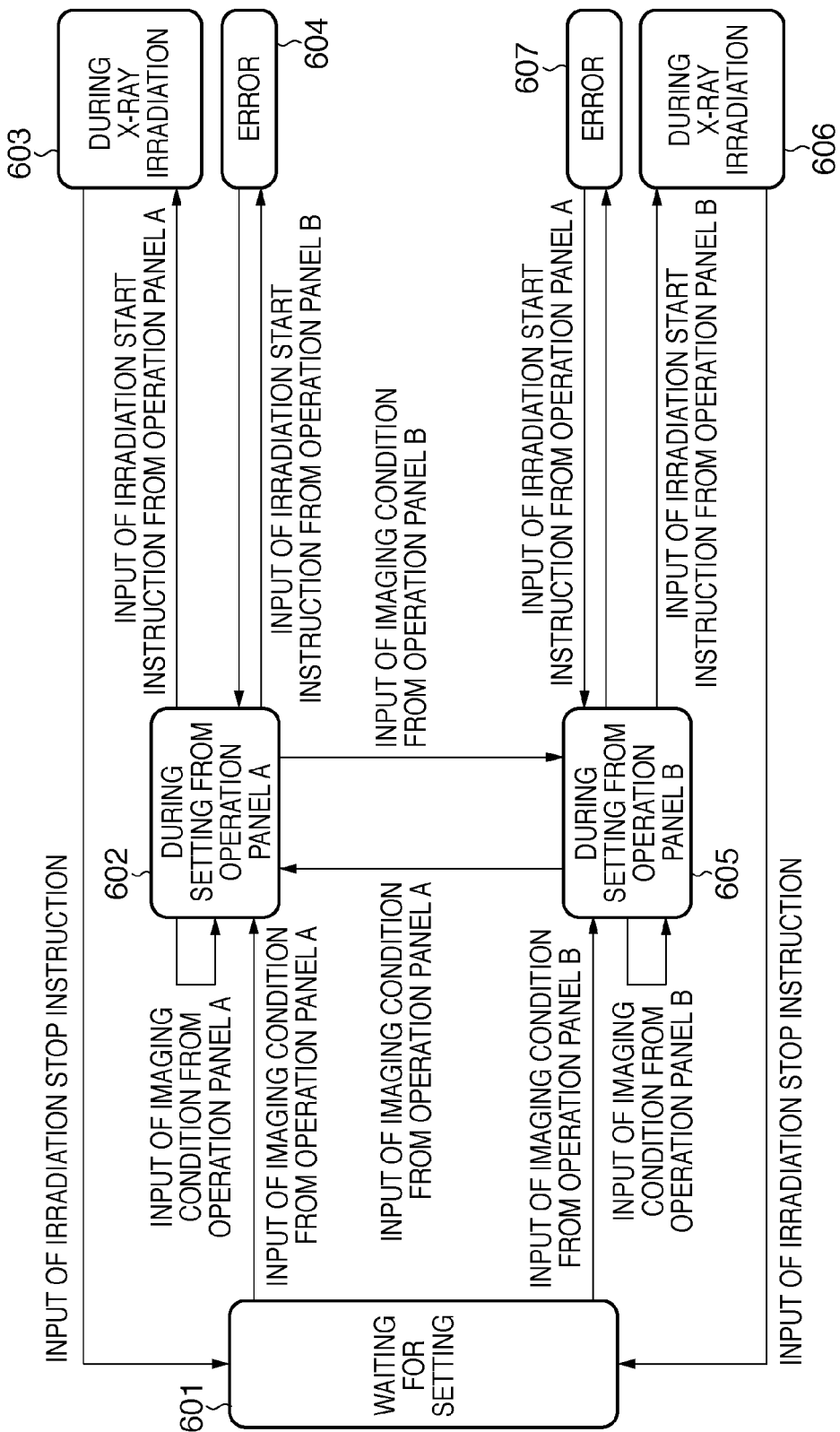
FIG. 6 is a view showing the state transition associated with control operations in an X-ray image diagnosis apparatus 100.

FIG. 6 is a view showing the state transition of control operations in the X-ray image diagnosis apparatus 100 according to this embodiment. Note that states 601 to 607 in FIG. 6 respectively correspond to the states 401 to 407 in FIG. 4.

In the setting wait state 601, when an imaging condition is input from the operation panel A 116 (step S503), the state transitions to the setting state 602.

In the setting state 602, if an imaging condition is input from the operation panel A 116, the input is normally processed. In contrast, if an imaging condition is input from the operation panel B 133 (step S506), the state transitions to the setting state 605 of the operation panel B 133.

If an irradiation start instruction (step S510) is input from the operation panel A 116, the state transitions to the X-ray irradiating state 603. When imaging (step S512) is complete, the state transitions to the setting wait state 601 again. In addition, if an irradiation start instruction (step S514) is input from the operation panel B 133, the state transitions to the error state 604 and returns to the setting state 602 again.

In the setting wait state 601, when an imaging condition is input from the operation panel B 133, the state transitions to the setting state 605 of the operation panel B 133. In this case, as in the setting state 602, when an imaging condition is input from the operation panel B 133, the input is normally executed. When an imaging condition is input from the operation panel A 116, the state transitions to the setting state 602 of the operation panel A 116.

When an irradiation start instruction is input from the operation panel B 133, the state transitions to the X-ray irradiating state 606. When imaging is complete, the state transitions to the setting wait state 601 again. When an irradiation start instruction is input from the operation panel A 116, the state transitions to the error state 607 and then returns to the setting state 605.

As is obvious from the above description, the X-ray image diagnosis apparatus according to this embodiment is configured such that every time an imaging condition is input, the operation right is re-set in the operation panel from which the imaging condition has been input. The apparatus is configured not to accept the input of an irradiation start instruction from the operation panel in which the operation right is not set. The apparatus is also configured to accept a control operation other than the input of an irradiation start instruction.

This makes it possible to avoid the situation in which the apparatus starts imaging under an unintended imaging condition.

Consequently, this can ensure convenience for operators while avoiding the risk of excessively exposing an object to X-rays.

[Third Embodiment]

The first and second embodiments are configured such that when the operation right is set in a given operation panel, the apparatus restricts the input of any imaging condition or irradiation start instruction from another operation panel in which the operation right is not set. However, the present invention is not limited to this arrangement.

If the apparatus keeps restricting a control operation on another operation panel as in the first and second embodiments, it may restrict even a control operation to be performed in an emergency. Depending on the use case or situation of the X-ray image diagnosis apparatus, there can be a case in which it is necessary to accept even a control operation from an operation panel on which a control operation is restricted.

The third embodiment will therefore exemplify an arrangement configured to further improve the usability of an X-ray image diagnosis apparatus while avoiding the risk of starting imaging under unintended imaging conditions.

Figure 7:
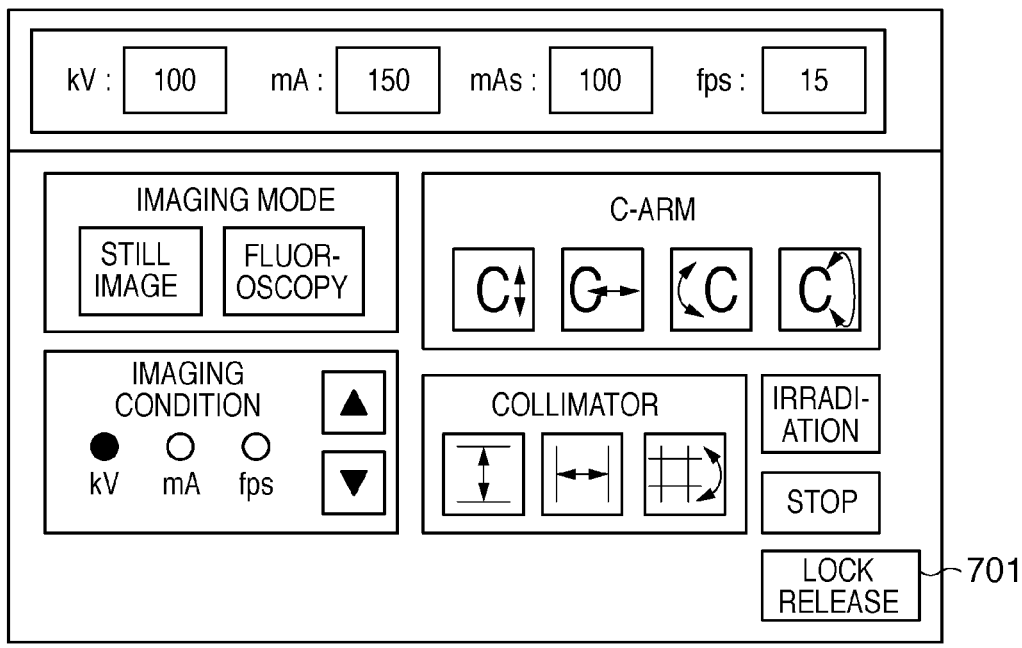
FIG. 7 is a view showing an example of a window displayed on a monitor forming an operation panel A 116 or operation panel B 113 in an X-ray image diagnosis apparatus according to the third embodiment of the present invention.

FIG. 7 is a view showing an example of a window displayed on a monitor forming an operation panel A 116 or operation panel B 133 in the X-ray image diagnosis apparatus according to this embodiment.

The window shown in FIG. 7 differs from the window shown in FIG. 2 (a window on the X-ray image diagnosis apparatus according to the first embodiment) in that the window in FIG. 7 additionally has a lock release button 701.

The lock release button 701 is a button for releasing the restriction of a control operation on one of the operation panel A 116 and the operation panel B 133 which is restricted from being used to input an imaging condition or irradiation start instruction.

Assume that the X-ray image diagnosis apparatus is in the setting state 402 or 405 in FIG. 4 or the setting state 602 or 605 in FIG. 6. In this case, when the operator presses the lock release button 701, the restriction is released to allow the input of an imaging condition or irradiation start instruction.

Figure 8:
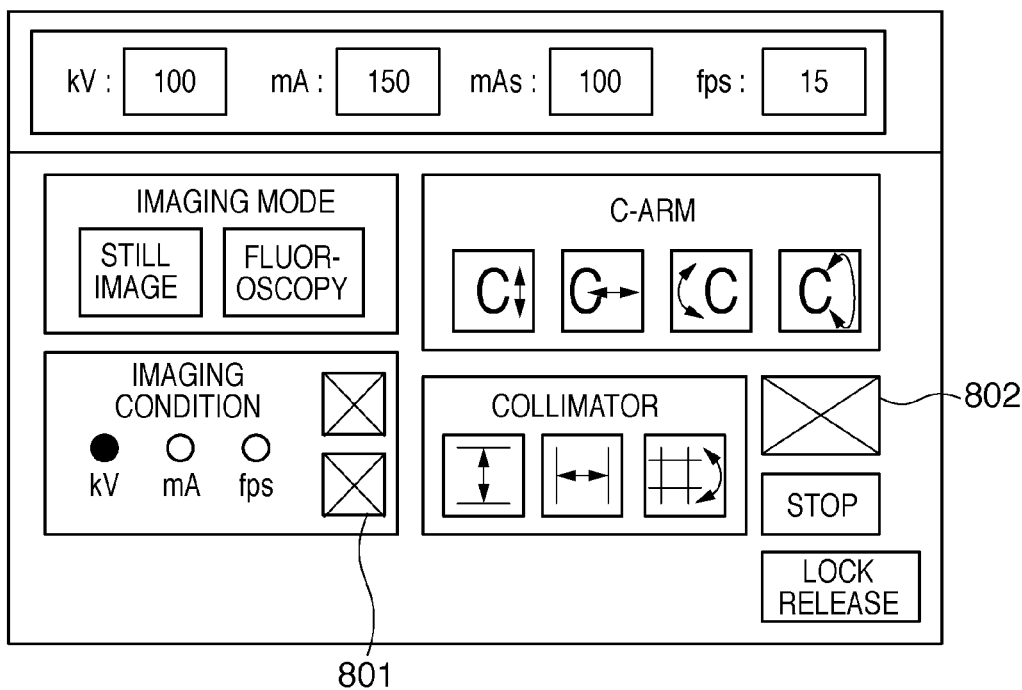
FIG. 8 is a view showing another example of the window displayed on the monitor forming the operation panel A 116 or operation panel B 113 in the X-ray image diagnosis apparatus according to the third embodiment of the present invention.

FIG. 8 is a view showing another example of the window displayed on a monitor forming the operation panel A 116 or operation panel B 133 in the X-ray image diagnosis apparatus according to this embodiment.

The window shown in FIG. 8 differs from the window shown in FIG. 2 in that the window in FIG. 8 additionally has the lock release button 701. Another difference is that while the apparatus restricts the input of any imaging condition or irradiation start instruction from an operation panel, the mark "X" 801 or 802 is displayed on the corresponding button. Executing such display control allows the operator to easily check what kind of control operation is currently restricted on the operation panel. In addition, when the operator presses the lock release button 701 to release this restriction, he/she can check it.

As is obvious from the above description, the X-ray image diagnosis apparatus according to this embodiment is provided with the lock release button in consideration of an emergency and the like while reducing the risk of performing imaging under unintended imaging conditions. In addition, this apparatus is configured to clearly demonstrate the control operation that is restricted on an operation panel.

This makes it possible to further improve the usability of the apparatus for the operator.

[Other Embodiments]

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-198619 filed on Jul. 31, 2008, which is hereby incorporated by reference herein in its entirety.

What is claimed is:

1. An X-ray imaging apparatus which irradiates an object with X-rays and processes an X-ray image obtained by imaging the object, the apparatus comprising:
   a reception unit configured to receive a radiographic parameter which is input via an operation unit;
   a determination unit configured to determine an operation unit from a plurality of operation units, including a first operation unit and a second operation unit, via which the received radiographic parameter has been input;
   a setting unit configured to set an operation right to the first operation unit if it is determined that the received radiographic parameter has been input via the first operation unit, and configured to set an operation right to the second operation unit if it is determined that the received radiographic parameter has been input via the second operation unit; and
   a restriction unit configured to restrict performance of imaging based on a radiographic parameter input via an operation unit other than the operation unit to which the operation right has been set using said setting unit.

2. The apparatus according to claim 1, wherein said restriction unit restricts reception of a start instruction to start X-ray irradiation which is input via an operation unit other than the operation unit to which the operation right is set using the setting unit.

3. The apparatus according to claim 1, wherein said restriction unit restricts reception of the radiographic parameter which is input via an operation unit other than the operation unit to which the operation right is set using the setting unit.

4. The apparatus according to claim 1, wherein, when imaging of the object is complete after imaging is started in accordance with a start instruction to start X-ray irradiation, said restriction unit releases the restriction.

5. The apparatus according to claim 1, wherein, when a release instruction is input via an operation unit, said restriction unit releases the restriction.

6. The apparatus according to claim 1, wherein, when a release instruction is input via an operation unit, said restriction unit releases the restriction on an operation unit from which the release instruction is input.

7. The apparatus according to claim 1, further comprising a display control unit configured to perform control to display, on an operation unit from which reception is restricted by said restriction unit, operation performed on the operation unit.

8. The apparatus according to claim 1, wherein the radiographic parameter includes parameters and instructions used for controlling an X-ray sensor or for controlling an X-ray tube.

9. The apparatus according to claim 1, wherein said determination unit determines an operation unit from the plurality of operation units via which the radiographic parameter first received by said reception unit is input.

10. The apparatus according to claim 9, wherein said restriction unit restricts the control of at least one of an X-ray sensor unit for imaging and an X-ray generator unit for X-ray irradiation.

11. The apparatus according to claim 1, wherein when an operation right is set to a first operation unit and a radiographic parameter is received from a second operation unit, said setting unit sets the operation right to the second operation unit instead of the first operation unit, and said restriction unit restricts initiation of X-ray irradiation of an X-ray generator based on a start instruction to start X-ray irradiation which is received from operation units other than the second operation unit.

12. The apparatus according to claim 1, wherein when said reception unit receives a parameter used for controlling a C-arm or a collimator of an X-ray generator from operation units to which the operation right is not set, said restriction unit does not restrict control of the C-arm or the collimator.

13. The apparatus according to claim 1, wherein, if an operation right is set to neither the first operation unit nor the second operation unit, said setting unit sets the operation right to the first operation unit in response to the determination that the received radiographic parameter is input via the first operation unit, and sets the operation right to the second operation unit in response to the determination that the received radiographic parameter is input via the second operation unit.

14. A control method for application to an X-ray imaging apparatus which irradiates an object with X-rays and processes an X-ray image obtained by imaging the object, the method comprising steps of:
   receiving a radiographic parameter, which is input via an operation unit;
   determining via which operation unit, including a first operation unit and a second operation unit, of plural operation units the parameter has been input;
   setting an operation right to the first operation unit if it is determined that the received radiographic parameter has been input via the first operation unit, and to the second operation unit if it is determined that the received radiographic parameter has been input via the second operation unit; and
   restricting performance of imaging based on a radiographic parameter input via an operation unit other than the operation unit to which the operation right is set.

15. A non-transitory computer-readable storage medium which stores a program for causing a computer to execute a control method defined in claim 14.

16. The method according to claim 14, wherein the radiographic parameter includes parameters and instructions used for controlling an X-ray sensor or for controlling an X-ray tube.

17. An X-ray image diagnosis apparatus which irradiates an object with X-rays and processes a radiographed image obtained by imaging the object, said apparatus comprising:

a reception unit configured to receive a radiographic parameter which is input via an operation unit;

a discrimination unit configured to discriminate, when said reception unit receives the radiographic parameter, from which operation unit of two or more operation units the parameter has been received; and a restriction unit configured to restrict performance of imaging based on a radiographic parameter received from an operation unit other than the operation unit discriminated by said discrimination unit, wherein, when a release instruction is input via an operation unit, said restriction unit releases the restriction on an operation unit from which the release instruction is input.

18. An X-ray image diagnosis apparatus which irradiates an object with X-rays and processes a radiographed image obtained by imaging the object, said apparatus comprising:

a reception unit configured to receive a radiographic parameter which is input via an operation unit;

a determination unit configured to determine an operation unit from among a plurality of operation units, including a first operation unit and a second operation unit, via which the received radiographic parameter has been input;

a setting unit configured to set an operation right to the first operation unit if it is determined that the received radiographic parameter has been input via the first operation unit, and configured to set an operation right to the second operation unit if it is determined that the received radiographic parameter has been input via the second operation unit; and a restriction unit configured to restrict performance of imaging based on a radiographic parameter input via an operation unit other than the operation unit to which the operation right is set using said setting unit, wherein the radiographic parameter is at least one of parameters and instructions used for controlling an X-ray sensor or for controlling an X-ray tube.

19. An X-ray image diagnosis apparatus which irradiates an object with X-rays and processes a radiographed image obtained by imaging the object, said apparatus comprising:

a reception unit configured to receive a radiographic parameter which is input via an operation unit;

a determination unit configured to determine an operation unit from among a plurality of operation units via which the received radiographic parameter has been input;

a setting unit configured to set an operation right to the operation unit determined by said determination unit; and a restriction unit configured to restrict performance of imaging based on a radiographic parameter input via an operation unit other than the operation unit to which the operation right is set by said setting unit, wherein, when the reception unit receives a parameter used for controlling a C-arm or a collimator of an X-ray generator from an operation unit to which an operation right is not set, said restriction unit does not restrict controlling of the C-arm or the collimator.

20. An X-ray imaging apparatus which irradiates an object with X-rays and processes an X-ray image obtained by imaging the object, the apparatus comprising:

a reception unit configured to receive a radiographic parameter which is input via an operation unit;

a determination unit configured to determine an operation unit from a plurality of operation units including a first operation unit and a second operation unit via which the received radiographic parameter has been input;

a setting unit configured to set an operation right to the first operation unit if said determination unit determines that a radiographic parameter has been input via the first operation unit, and configured to set an operation right to the second operation unit if said determination unit determines that a radiographic parameter has been input via the second operation unit; and a restriction unit configured to restrict performance of imaging based on a radiographic parameter input via an operation unit other than the operation unit to which the operation right has been set using said setting unit, wherein, when an operation right is set to a first operation unit and a radiographic parameter is received from a second operation unit, said setting unit sets the operation right to the second operation unit instead of the first operation unit, and said restriction unit restricts initiation of X-ray irradiation of an X-ray generator based on a start instruction to start X-ray irradiation which is received from operation units other than the second operation unit.

\* \* \* \* \*